United States Patent [19]

Wu et al.

[11] Patent Number: 4,689,398

[45] Date of Patent: Aug. 25, 1987

[54] HTLV TEST USING SYNTHETIC PEPTIDES

[75] Inventors: Ying-Jye Wu, Reading; Joseph L. W. Chan, Quincy, both of Mass.

[73] Assignee: Ortho Diagnostic Systems Inc., Raritan, N.J.

[21] Appl. No.: 622,430

[22] Filed: Jun. 20, 1984

[51] Int. Cl.$^4$ .............................................. C07K 7/08
[52] U.S. Cl. ................................................ 530/327
[58] Field of Search ........................... 514/12; 530/327

[56] References Cited

U.S. PATENT DOCUMENTS 4,554,101 11/1985 Hopp ................................... 514/12

OTHER PUBLICATIONS

Proc. Natl. Acad. Sci., vol. 80, pp. 3618–3622 (1983).
Biochemistry, 13 (1974), 222–245.

Primary Examiner—Delbert R. Phillips
Attorney, Agent, or Firm—Mark A. Hofer

[57] ABSTRACT

Synthetic peptides simulating hydrophilic envelope regions and antibodies specific therefor useful for the detection of Human T-cell Leukemia virus or naturally occurring immunoglobulin against HTLV.

8 Claims, 1 Drawing Figure

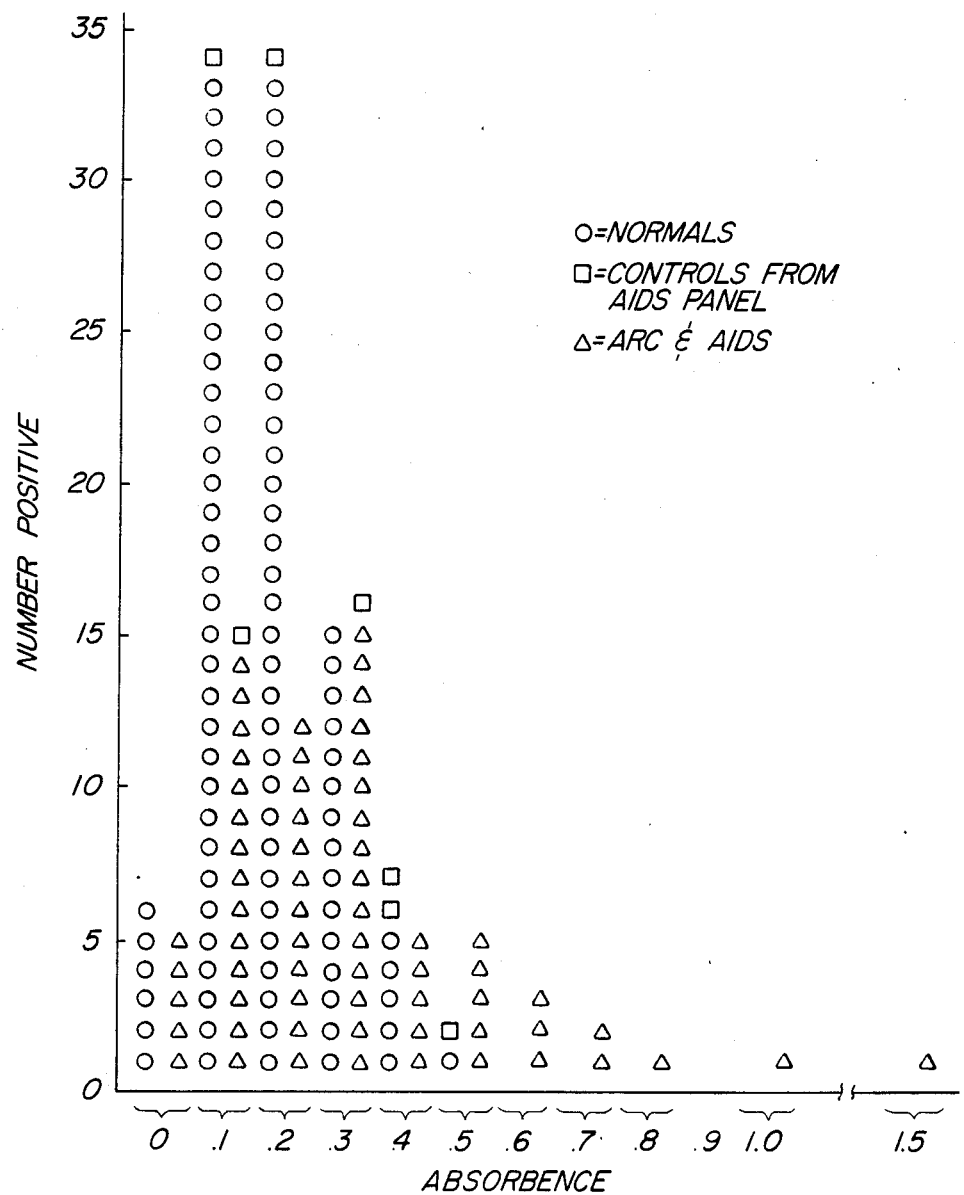

HTLV TEST USING SYNTHETIC PEPTIDES

FIELD OF THE INVENTION

This invention is related to assays utilizing synthetic peptides and more particularly, relates to assays for the detection of antibodies specific for Human T-cell Leukemia Virus envelope.

BACKGROUND OF THE INVENTION

HTLV I or Human T-cell Leukemia Virus Type I, has been identified as a causative organism for at least some forms of leukemias. This virus has been the subject of much study and has also been linked to Acquired Immune Deficiency Syndrome (AIDS). Recent studies have indicated the Type I virus is closely related to HTLV Type III virus perhaps even more closely linked to AIDS based on the work of Dr. Robert Gallo et al. of the National Cancer Institute Laboratory. Type III virus is probably the same as the LMV virus identified by the research group at the Pastuer Institute working in conjunction with the NCI; work to verify this is presently underway.

AIDS is a devastating disease wherein individuals become immunologicaly incompetent and in virtually all cases, the prognosis is certain death since at present there is no adequate treatment. Although the genesis of the disease is still the subject of much speculation, it is known that AIDS and similar virally caused conditions may be acquired by the transfusion of blood from an infected donor. Complicating the diagnosis of AIDS related diseases is the fact that these diseases are often characterized by significant incubation periods, generally on the order of two years before symptoms are expressed.

It is an object of the present invention to provide a highly diagnostic test whereby persons having such disease or having been immunologically exposed to the causative organisms may be identified and diagnosed well prior to the appearance of symptomatic conditions.

Owing to the uncertain and apparently highly infective nature of these viral organisms, research has been severely hampered by the need to take extraordinary measures to contain the virus and prevent its transmission to otherwise healthy persons. Indeed, the organism has been surrounded with such a stigma that it is very difficult and often impossible to find persons of the required caliber willing to engage in the research or manufacture of tests which employ some portion of the virus, despite its apparent deactivation.

It is a related object of the present invention to provide tests which do not rely upon deactivated virus and accordingly pose no threat for infection.

Similarly, any conventional vaccine developed utilizing deactivated virus will be difficult to manufacture. Once manufactured, it will be difficult to test due to the understandable reluctance of any volunteers. These difficulties, in combination with the long infectivity times, the infectious nature of the disease, and the present impossibility of identifying nonpreviously exposed persons or healthy "controls" will effectively prevent or unduly delay the procurement of requisite marketing approvals.

It is still another related object of the present invention to provide materials which pose no threat of infectivity but which will nonetheless be useful as vaccines.

SUMMARY OF THE INVENTION

In accordance with the principles and objects of the present invention, there are provided synthetic peptides which, individually or in combination, may be utilized to identify patient fluid samples containing HTLV specific immunoglobulin. The synthetic peptides provided herein mimic specific, selected portions of HTLV viral envelope proteins and accordingly contain no genetic information which can pose an infective threat. Thus, these synthetic peptides may be used, not only immunodiagnostically, but also as vaccines for the generation of antibodies specific to HTLV envelope. The vaccinated individual thus becomes immunologically more competent to deal with any future HTLV threatened infection.

DETAILED DESCRIPTION OF THE INVENTION AND BEST MODE

The use of synthetic peptides to raise antibodies of predetermined binding specificity and other biological applications such as diagnostic assays and the like, has been previously reported by Dr. Richard Lerner of the Scripps Institute in Nature 299:592 (1982). Such methods have, however, previously been hampered in that the antibodies raised by the injection of synthetic peptides into animals often do not correspond to, are not blocked by, and/or do not block naturally raised antibodies against the corresponding antigen or organism which the synthetic peptide has been designed to simulate. Accordingly, the usefulness of synthetic peptides has, to date, generally been severely limited since the naturally occurring antibodies and the synthetic peptide raised antibodies somehow react differently or recognize different antigenic determinates. Thus, the presence of reactivity by one antibody could not be used to predict or detect the presence of the other antibody.

It has been surprisingly discovered by the inventors hereof, that such is not the case with certain selected HTLV envelope regions, particularly with the polypeptide sequences of the present invention.

The entire HTLV Type I genomic sequence was published by Seiki et al. in Proc. Natl. Acad. Sci., Vol. 80:3618–3622 (June 1983). This genomic sequence, of course, contains all of the information necessary in order to create a complete and infective virus. There was, however, prior to the invention hereof, no indication as to which portions of this sequence corresponded to the immunologically relevant envelope antigenic determinants or whether the generation of such determinants via the creation of synthetic peptides could immunologically raise antibodies comparable to those naturally occurring against the complete, infective HTLV particle.

The preferred sequences of the instant invention were selected by a combination of the following procedures. The hydropathicity of the envelope gene was calculated using the default values supplied by Hopp and Woods as described in Hopp et al., "Prediction of Protein Antigenic Determinants From Amino Acid Sequences", Proc. Natl. Acad. Sci. 78(6):3824–3828 (June 1981). Using those procedures, the following values were derived:

| | | | | | |
|---|---|---|---|---|---|
| A | −.499 | T | −.399 | Q | .200 |
| G | 0 | D | 3.000 | W | −3.399 |
| M | −1.299 | I | −1.799 | F | −2.499 |

| | -continued | | | | |
|---|---|---|---|---|---|
| S | .300 | P | 0 | L | −1.799 |
| C | −.999 | V | −1.499 | R | 3.000 |
| H | −.499 | E | 3.000 | Y | −2.299 |
| N | .200 | K | 3.000 | | | where, for the HTLV envelope gene:

| | AMINO ACID DISTRIBUTION | |
|---|---|---|
| NAME | NUMBER | PERCENTAGE |
| A = Alanine | 30 | 6.1 |
| C = Cysteine | 18 | 3.7 |
| D = Aspartic Acid | 14 | 2.9 |
| E = Glutamic Acid | 10 | 2.0 |
| F = Phenylalanine | 17 | 3.5 |
| G = Glycine | 25 | 5.1 |
| H = Histidine | 16 | 3.3 |
| I = Isoleucine | 22 | 4.5 |
| K = Lysine | 16 | 3.3 |
| L = Leucine | 73 | 14.9 |
| M = Methionine | 3 | .6 |//
| | -continued | |
| | AMINO ACID DISTRIBUTION | |
| NAME | NUMBER | PERCENTAGE |
| N = Asparagine | 20 | 4.1 |
| P = Proline | 47 | 9.6 |
| Q = Glutamine | 23 | 4.7 |
| R = Arginine | 16 | 3.3 |
| S = Serine | 54 | 11.0 |
| T = Threonine | 26 | 5.3 |
| V = Valine | 26 | 5.3 |
| W = Tryptophan | 13 | 2.7 |
| Y = Tyrosine | 19 | 3.9 |

Molecular weight for this polypeptide = 53954.73.

The hydropathicity average at residue i was calculated across 6 residues from i−3 through and including i+2. The hydropathicity maximum was 1.666667 at residue No. 351. The hydropathicity of the amino acid sequences was then analyzed using the IntelliGenetics software from IntelliGenetics, Inc. to derive regions of hydrophobicity and hydrofilicity, and the values in Table 1 were derived.

TABLE 1

```
                     −1          0           1
                      !          !           !
 1                              M*********
 2                        ***   G
 3+                   ********  K
 4                    ********  F
 5                      ******  L
 6                  **********  A
 7        ************************  T
 8         ***********************  L
 9         ***********************  I
10     *****************************  L
11     *****************************  F
12     *****************************  F
13      ****************************  Q
14         *************************  F
15           ***********************  C
16             *********************  P
17      ****************************  L
18              ********************  I
19                        ********    F
20                 ******************  G
21−                       *********    D
22                            ****     Y
23                              S***
24                              P
25                    **********       S
26                         *****       C
27                   ***********       C
28                  ************       T
29          ******************         L
30             ***************         T
31              **************         I
32                *************        G
33                     ********        V
34                ************         S
35                  **********         S
36                   *********         Y
37+                             H***
38                              S**
39+                           * K
40                              P*****
41                              C******
42                              N****
43                         ***  P
44                         ***  A
45                        ****  Q
46                      ******  P
47                      ******  V
48                ************  C
49                ************  S
50       **********************  W
51                   *********   T
52                  **********   L
53−               ***************  D
```

TABLE 1-continued

| | | |
|---|---|---|
| 54 | ********* | L |
| 55 | ************* | L |
| 56 | ******* | A |
| 57 | ******************* | L |
| 58 | *** | S |
| 59 | | A* |
| 60— | | D* |
| 61 | | Q* |
| 62 | | A* |
| 63 | | L*** |
| 64 | ***** | Q |
| 65 | ********* | P |
| 66 | ******** | P |
| 67 | * | C |
| 68 | ******* | P |
| 69 | *********** | N |
| 70 | *********** | L |
| 71 | ************** | V |
| 72 | ************** | S |
| 73 | ************** | Y |
| 74 | ************** | S |
| 75 | ************** | S |
| 76 | ************** | Y |
| 77+ | ******** | H |
| 78 | ****************** | A |
| 79 | ****************** | T |
| 80 | ****************** | Y |
| 81 | ******************* | S |
| 82 | ************************ | L |
| 83 | ****************************** | Y |
| 84 | *********************** | L |
| 85 | ************************ | F |
| 86 | ******************************* | P |
| 87+ | ************************ | H |
| 88 | ********** | W |
| 89 | | T**** |
| 90+ | | K**** |
| 91+ | | K****** |
| 92 | | P*********************** |
| 93 | | N************************* |
| 94+ | | R****************** |
| 95 | | N********* |
| 96 | | G********* |
| 97 | | G** |
| 98 | ************ | G |
| 99 | ************ | Y |
| 100 | ************ | Y |
| 101 | ************ | S |
| 102 | ******************* | A |
| 103 | *********** | S |
| 104 | | Y*** |
| 105 | | S** |
| 106— | | D |
| 107 | | P |
| 108 | | C** |
| 109 | | S********* |
| 110 | * | L |
| 111+ | * | K |
| 112 | ***** | C |
| 113 | ************ | P |
| 114 | ***** | Y |
| 115 | ****************** | L |
| 116 | ************* | G |
| 117 | ************* | C |
| 118 | ***************** | Q |
| 119 | ************ | S |
| 120 | *************** | W |
| 121 | ************* | T |
| 122 | ******************** | C |
| 123 | *********************** | P |
| 124 | ********** | Y |
| 125 | *********** | T |
| 126 | ************* | G |
| 127 | ************ | A |
| 128 | ***** | V |
| 129 | *** | S |
| 130 | ********** | S |
| 131 | ****************** | P |
| 132 | ***** | Y |
| 133 | ************ | W |
| 134+ | *************** | K |
| 135 | *************** | F |

TABLE 1-continued

| # | | AA |
|---|---|---|
| 136 | | Q |
| 137+ | | H**** |
| 138− | *** | D |
| 139 | *** | V |
| 140 | **** | N |
| 141 | ** | F |
| 142 | ** | T |
| 143 | ** | Q |
| 144− | ** | E |
| 145 | | V************* |
| 146 | | S********* |
| 147+ | | R********* |
| 148 | **** | L |
| 149 | | N |
| 150 | ***** | I |
| 151 | *************** | N |
| 152 | ****************** | L |
| 153+ | ****************** | H |
| 154 | *** | F |
| 155 | ******* | S |
| 156+ | * | K |
| 157 | ******* | C |
| 158 | | G |
| 159 | ******* | F |
| 160 | *************** | P |
| 161 | ***************** | F |
| 162 | ********************** | S |
| 163 | ******************* | L |
| 164 | ************ | L |
| 165 | ****** | V |
| 166− | ******* | D |
| 167 | ** | A |
| 168 | *** | P |
| 169 | | G********* |
| 170 | | Y |
| 171− | *** | D |
| 172 | ************ | P |
| 173 | ******************* | I |
| 174 | ****************** | W |
| 175 | ************************* | F |
| 176 | ***************************** | L |
| 177 | ************** | N |
| 178 | **** | T |
| 179− | | E*** |
| 180 | | P********* |
| 181 | | S*** |
| 182 | | Q**** |
| 183 | *** | L |
| 184 | **** | P |
| 185 | ****** | P |
| 186 | ****** | T |
| 187 | ** | A |
| 188 | ****** | P |
| 189 | ************ | P |
| 190 | *********** | L |
| 191 | *********** | L |
| 192 | ********** | P |
| 193+ | ********** | H |
| 194 | ********** | S |
| 195 | | N*** |
| 196 | | L* |
| 197− | * | D |
| 198+ | ******* | H |
| 199 | | I |
| 200 | | L***** |
| 201− | ** | E |
| 202 | ***** | P |
| 203 | | S |
| 204 | ***** | I |
| 205 | ***** | P |
| 206 | **** | W |
| 207+ | | K*** |
| 208 | | S*** |
| 209+ | * | K |
| 210 | | L****** |
| 211 | ****** | L |
| 212 | *********** | T |
| 213 | ******************** | L |
| 214 | ******************* | V |
| 215 | *************** | Q |
| 216 | ***************** | L |
| 217 | ************** | T |

TABLE 1-continued

| # | | AA |
|---|---|---|
| 218 | ******** | L |
| 219 | ********** | Q |
| 220 | ***** | S |
| 221 | ********* | T |
| 222 | ****** | N |
| 223 | ********* | Y |
| 224 | *************** | T |
| 225 | ****************** | C |
| 226 | ********************** | I |
| 227 | ****************** | V |
| 228 | ********** | C |
| 229 | | I |
| 230− | | D*** |
| 231+ | | R******** |
| 232 | | A***** |
| 233 | | S************ |
| 234 | | L** |
| 235 | *************** | S |
| 236 | *************** | T |
| 237 | ******************* | W |
| 238+ | ******************** | H |
| 239 | ************************** | V |
| 240 | ************************ | L |
| 241 | **************** | Y |
| 242 | *************** | S |
| 243 | *************** | P |
| 244 | ******** | N |
| 245 | ***** | V |
| 246 | ******* | S |
| 247 | ****** | V |
| 248 | ***** | P |
| 249 | | S |
| 250 | | S |
| 251 | | S** |
| 252 | | S** |
| 253 | *** | T |
| 254 | ********* | P |
| 255 | ****************** | L |
| 256 | ****************** | L |
| 257 | *************** | Y |
| 258 | ******************** | P |
| 259 | ***************** | S |
| 260 | ***************** | L |
| 261 | ********** | A |
| 262 | ************ | L |
| 263 | ************ | P |
| 264 | ********* | A |
| 265 | ************** | P |
| 266+ | ********* | H |
| 267 | *************** | L |
| 268 | ************ | T |
| 269 | ******************** | L |
| 270 | ***************** | P |
| 271 | ************************ | F |
| 272 | *********************** | N |
| 273 | ****************** | W |
| 274 | ********************** | T |
| 275+ | ********************** | H |
| 276 | ************* | C |
| 277 | *** | F |
| 278− | ** | D |
| 279 | ***** | P |
| 280 | ** | Q |
| 281 | | I*** |
| 282 | ********** | Q |
| 283 | *************** | A |
| 284 | ************** | I |
| 285 | ******** | V |
| 286 | ********* | S |
| 287 | ********** | S |
| 288 | ****** | P |
| 289 | * | C |
| 290+ | * | H |
| 291 | ******* | N |
| 292 | ************* | S |
| 293 | *************** | L |
| 294 | ************* | I |
| 295 | ************* | L |
| 296 | *********************** | P |
| 297 | **************** | P |
| 298 | ***************** | F |
| 299 | ********** | S |

TABLE 1-continued

```
300         *********   L
301         **************   S
302         *******   P
303         ********   V
304         ********   P
305         *********   T
306         ********   L
307                    G***
308                    S***
309+                   R*************
310                    S******************************
311+                   R************************
312+                   R********************
313                    A************
314                    V*******
315              **    P
316         ***************   V
317    ********************   A
318   **************************   V
319  *****************************   W
320    ********************   L
321    *******************   V
322   **********************   S
323         ****************   A
324         ***************   L
325         **********   A
326         **************   M
327         ***********   G
328         **********   A
329         **********   G
330         *******   V
331         *******   A
332         **********   G
333         **********   G
334         *******   I
335         *****   T
336         *********   G
337         ********   S
338         *******   M
339         ********   S
340         *******   L
341         ********   A
342                    S***
343                    G***
344+                   K***
345                    S
346              **    L
347                    L******
348+          ******   H
349−                   E*
350                    V**************
351−                   D****************************
352+                   K***********************
353−                   D****************
354                    I********************
355                    S********
356            *       Q
357         *********   L
358         *****   T
359         **********   Q
360         ****************   A
361              **    I
362             *      V
363+            ***    K
364                    N******
365+                   H*************
366+                   K***********
367             *      N
368                    L*****
369                    L**
370+        *******   K
371         *******   I
372         *********   A
373         *****   Q
374         ***************   Y
375         ********   A
376         *******   A
377                    Q
378                    N***************
379+                   R***************
380+                   R*************
381                    G******************
```

} i

} ii

TABLE 1-continued

| # | | AA |
|---|---|---|
| 382 | | L*************** |
| 383− | | D* |
| 384 | ************* | L |
| 385 | ********************* | L |
| 386 | ********* | F |
| 387 | ****************** | W |
| 388− | ************ | E |
| 389 | ******* | Q |
| 390 | ***** | G |
| 391 | | G* |
| 392 | | L* |
| 393 | | C |
| 394+ | ***** | K |
| 395 | ***** | A |
| 396 | | L******** |
| 397 | | Q*********** |
| 398− | | E |
| 399 | | Q********** |
| 400 | | C******** |
| 401+ | | R******* |
| 402 | | F |
| 403 | ***** | P |
| 404 | **** | N |
| 405 | ************ | I |
| 406 | **** | T |
| 407 | ***** | N |
| 408 | ********** | S |
| 409+ | ***** | H |
| 410 | ********* | V |
| 411 | *************** | P |
| 412 | *************** | I |
| 413 | ***** | L |
| 414 | | Q******* |
| 415− | E******* | |
| 416+ | | R************ |
| 417 | | P************ |
| 418 | | P******************** |
| 419 | | L************ |
| 420− | | E************ |
| 421 | | N******** |
| 422+ | | R*** |
| 423 | | V******* |
| 424 | * | L |
| 425 | *********** | T |
| 426 | ******************** | G |
| 427 | ********************* | W |
| 428 | **************** | G |
| 429 | ************************ | L |
| 430 | **************** | N |
| 431 | ********** | W |
| 432− | ********** | D |
| 433 | ********** | L |
| 434 | ********** | G |
| 435 | | L |
| 436 | ****************** | S |
| 437 | ************** | Q |
| 438 | ****** | W |
| 439 | | A******* |
| 440+ | | R***** |
| 441− | | E |
| 442 | | A********* |
| 443 | | L********* |
| 444 | | Q* |
| 445 | ************ | T |
| 446 | *********** | G |
| 447 | *********** | I |
| 448 | ***************** | T |
| 449 | ***************** | L |
| 450 | ********************** | V |
| 451 | ********************** | A |
| 452 | *************************** | L |
| 453 | ************************** | L |
| 454 | ************************** | L |
| 455 | ***************************** | L |
| 456 | ***************************** | V |
| 457 | ************************** | I |
| 458 | ******************* | L |
| 459 | *************** | A |
| 460 | ************** | G |
| 461 | ************** | P |
| 462 | ************** | C |
| 463 | **** | I | iii (bracket covering rows 413–422)

TABLE 1-continued

```
464              *** L
465+        ******** R
466                  Q**
467                  L*****
468+                 R*****
469+              ** H
470               ** L
471                  P**********
472              *   S
473+                 R********
474                  V*******
475+                 R*******
476                  Y****
477        **********P
478+             ***** H
479        ******************* Y
480        ****************** S
481           ******** L
482            ******* I
483+                 K*******
484                  P*******
485-                 E************
486                  S*************
487                  S******
488                  L*******
489           ******
           !         !         !
          -1         0         1
```

"+" or "—" after a residue number indicates a charged residue.
The residue(s) "." are not included in calculatung average hydropathicity values.

Accordingly, the three hydrophilic regions indicated in Table I by brackets were selected to make synthetic peptides having the following primary structures:
Cys-His-Glu-Val-Asp-Lys-Asp-Ile-Ser-Gln-Leu-Gly (i)
Cys-Ala-Gln-Asn-Arg-Arg-Gly-Leu-Asp-Leu-Leu-Gly (ii)
Cys-Ile-Leu-Gln-Glu-Arg-Pro-Pro-Leu-Glu-Asn-Gly (iii)

The HTLV envelope gene secondary structure was also calculated using the methods of Chou and Fasman (Biochemistry 13 (1974) 222; Adv Enzymol (1978) 47 45; Annu Rev Biochem (1978) 47 251):

```
           10         20         30         40         50         60         70
MGKFLATLI LFFQFCPLI FGDYS PS CCTLTI GVS S YHS KP CNP AQP VCSWTLLL ALS ADQALQPPCPNL
AAAAAAAA                                          AAAAAAAAAAAAAAA
    BBBBBBBBBBBBBBBB     BBBBBBB          BBBBB BBBBBB               BBBB
            T?T? TTTTTTT          TTTTT? TTTTTTT? TTTTT       TTTT        TTTTTT 80         90        100        110        120        130        140
VS YS S YHATYS LYLFP HWTKKP NRNGGGYYS AS YS DPCS LKCP YLGCQSWTCP YTGAVS S PYWKFQHDVN
               AAAAAA                                                  AAAAAA
B    BBBBBBBBB                              BBBBB BBBBBB            BBBBBBBBB
TTTTTTT? T?      TTTT    TTTTTTTT    TTTTTTTT   TTTT TTTT TTTTT?    TTTT     T? T 150        160        170        180        190                  210
FTQEVS RLNI NLHFS KCGFPFS LL VDAP GYDP I WFLNTEP S QLPPTAP PLLP HS NLDH120CEP S I PWKS KL
    AAAAAAA           AAAAAAA                                AAAAAA  AAAAAA
BBB      BBBBBB         BBBBB       BBBBBBB                  BBBBBB       BB
?              TTTTTTT       TTTT? T?  T! TTTT  TTTTT? TTTTTTT      TTTT? TTTT 220        230        240        250        260        270        280
LTLVQLTLQS TNYTCI VCI DRAS LS TWHVLYS PNVS VPS S S S TPLLYPS LALPAPHLTLPFNWTHCFDPQ
                                                              AAAAAA        AAA
BBBBBBBBBBBBBBBBBBBB       BBBBBBBB       BBBBB            BBBBBBBB       BB
       TTTTT?   T? T?   T? T?     TTTT TTTTTT      TTTT      TTTT  TTTT? T? T? T
```

```
                  290         300         310         320        330        340         350
           I QAI VS S P CHNS LI LPPFS LS PVPTLGS RS RRAVP VAVWLVS AL AMGAGVAGGI TGSMS LAS GKS LLHEV
                                                                                              |<—

AAAA                                         AAAAAAAA                     AAAAAAA
           BBBBB     BBBBBBB                    BBBBBBBBBBB
           ?         TTTTTT      TTTT   T? T? TTTT                      T? TTTTTT? TT? T? TT 360         370         380         390        400        410         420
           DKDI SQLTQAI VKNHKNLLKI AQYAAQNRRGLDLLFWEQGGLCKALQEQCRFPNI TNS HVPI LQERPPLE
              ——>|                |<——>|                                     |<——>|

AAAAAAAAAAAA AAAAAAAAA AAAAAA AAAAAAAA AAAAAAAAAAAA        AAAAAA    AA
              BBBBBBBBB     BBBBB        BBBBBB                   BBBBBB BBBBB
           TTTT          TTTT    T? TTTT         TTTT             TTTT? TTTT 430         440         450         460        470        480
           NRVLTGWGLNWDLGLSQWAREALQTGI TLVALLLLVI LAGPCI LRQLRHLPSRVRYPHYSLI KPES SL
           |

AAAA          AAAAAAAAAA                         AAAAAA
           BBBBB BBBBB         BBBBBBBBBBBBBBBBBB BBBBBBB             BBBBB
              TTTTT? T?              T? T?            TTTT     TTTT TTTTT?   TTTT
``` where:
- AAAAAA = Alpha helix
- BBBBB = Beta sheet
- TTTT = Turn (turn frequency > = absTurnMin)
- T?T? = Other possible turn sites (turn frequency > relTurnMiMin)

As will be readily understood by those familiar with this algorithm, the secondary structures predicted are mere indications as there exists tremendous variability within proteins. Further, the secondary structure algorithm is still highly experimental. However, the complicated nature of the protein as demonstrated by numerous As, Bs and Ts at the three selected hydrophilic sites identified in Table 1 as i, ii and iii does seem to correlate with concepts of immunological reactivity.

The selected peptides were synthesized with a Beckman 990 peptide synthesizer and isolated from the resin using hydrogen fluoride HF apparatus. The synthetic peptides were separated and purified using gel columns and HPLC and the amino acid composition checked by identification of the peptides with reverse phase HPLC (High Performance Liquid Chromatography) methods. These methods have in recent publications become well-known to those skilled in the art and need not be reviewed here.

The synthetic peptides were then used to generate polyclonal antisera in rabbits via standard immunization techniques. Murine monoclonal antibodies were also raised against the three synthetic peptides using the hybridoma procedures substantially as set forth by Kohler and Milstein in Nature 225 (1974). Both the polyclonal and monoclonal antibodies demonstrated specific binding to each of its own peptides without cross-reaction with the other peptides.

The polyclonal and monoclonal antibodies were also capable of binding to disrupted and chemically fixed HTLV which was coated onto microtiter plates and obtained from Biotech Research Laboratories. Thus, these antibodies or fragments thereof, can also be used diagnostically in any of a number of well-known immunoassay formats.

Because the antibodies raised from the peptides of the present invention were surprisingly and unexpectedly capable of recognizing the native, intact HTLV, it was wondered whether naturally occuring antibodies, present in the serum of AIDS or leukemia patients, would also be capable of recognizing the peptides.

The three peptides were mixed and coated onto microtiter plates where they were fixed with methanol. Serum samples from known AIDS and ARC patients, from "Normals" and from "AIDS controls" were reacted therewith under suitable and conventional temperature, time and pH conditions conducive to immunological reactions. Unreacted components were removed and reacted antibodies were labeled indirectly by reaction with anti-human IgG having the enzyme label, horseradish peroxidase, attached thereto. The substrate o-phenylenediamene was added and resultant color development was monitored spectrophotometrically at about 400 nm. The results are presented in the FIGURE. Despite the obvious need to optimize the assay, it is clear that a useful test can be formulated using at least one or a combination of the peptides of the present invention. It must also be recognized that at present, there is no standard or accepted value against which to compare this data. Persons presently believed to be "Normal" may in fact be representative of the average person and that nearly everyone has been, at one time or another, exposed to AIDS causative organisms but has for unknown reasons, been successful in resisting the disease. Thus, it may be "Normal" to have been exposed and thus have developed immunological resistance.

Except for Epstein Barr nuclear antigens, this is the first time that a naturally occurring antibody reacts with synthetically raised peptides, or that antibodies raised against peptides react with intact virus. Due to the extremely close resemblance getween HTLV Type III and HTLV Type I, it is anticipated that the preferred synthetic peptides of the present invention will be equally applicable for the detection of either or both of these viruses. At most, the envelope regions of the two viruses will differ in only one or two amino acids. Such minor alterations of the synthetic peptides of the present invention are equally contemplated herein and are to be deemed equivalents. Further, it is possible that the critical regions, those actually recognized by the antibodies will only be a portion of the peptides described herein and these are also to be deemed equivalents.

The three synthetic peptides described may be used separately, however, due to the heterogeneity of antibodies naturally raised against invasive organisms, the preferred embodiments will employ a mixture of the synthetic peptides, all three in the most preferred embodiment, in order to maximize the detection of all possible natural antibodies against the HTLV virus. Although the relative proportions used in the described example were equal amounts of each synthetic peptide, optimization may indicate other proportions to be more advantageous. Optimization procedures are straightforward and well within the ken of the skilled investigator.

As will be readily comprehended by those skilled in the art, the synthetic peptides of the present invention may be formulated into a variety of heterogeneous and homogeneous immunoassay formats having either competitive or noncompetitive characteristics. The preferred embodiment utilizes the synthetic peptides immobilized onto a solid phase such as the surface of a microtiter well, and upon which the patient serum sample (or such other sample containing the antibodies or viral particles to be detected) may be conveniently reacted. Patient antibodies specific for HTLV virus, if present, will then react with the immobilized synthetic peptides. (Although a noncompetitive assay is described, it is to be understood the instant invention is not so limited and that competitive assays, e.g., competition of a supplied immunoglobulin or immunoglobulin fragment for the synthetic peptide in the presence of sample viral particles, is equally contemplated.) Unreacted components of the serum sample are then preferably removed in order to remove unwanted background and other sources of nonspecific binding. Thereafter, labeled anti-human immunoglobulin of polyclonal or monoclonal origin may be used in order to react with, and thus label the anti-HTLV human immunoglobulin, now attached to the synthetic peptide if present in the patient sample. Unreacted labeled anti-human immunoglobulin (aqueous phase) is then removed and label associated with either the solid phase or aqueous phase measured in accordance with well-known techniques. Such techniques will, of course, depend on the nature of the label used, for instance spectrophotometers or colorimeters may be employed to detect fluorescence, absorbance, etc. generated by chemiluminescent molecules, fluorescent molecules, absorbing dye molecules and the like. Equally contemplated is the generation and detection of product from the activity of an enzymatic label upon a reactant such as is associated with the so-called ELISA type methods. For instance, the enzyme horseradish peroxidase, was employed in the example. Other possible markers include light scattering particles, magnetic particles, isotopes, red blood cells, and synthetic and naturally occurring particles of both macro and micro dimensions.

It will be readily understood that due to the nature of the ongoing research, and the fact that full comprehension of AIDS and other related diseases is far from complete, the assay methods of the instant invention are qualitative in nature, i.e. the presence of HTLV specific antibody in a patient serum will be indicative of or prognostic evidence of AIDS or an AIDS like infection. This is because at present there are no standards against which to compare results and formulate a quantitative analysis. It is, however, anticipated that at some point in the future, the existance of a certain level of HTLV specific antibody may be regarded as normal without necessarily indicating the imminent onslaught of disease. At such time, and upon identification of this level, the synthetic peptides and assays of the present invention may be employed in a quantitative nature.

One skilled in the art will readily determine that based on the foregoing, minor modifications of the synthetic peptides or the antibodies specific therefor may be made along with numerous modifications to the virtually unlimited immunoassay formats available for use with the synthetic peptides or the antibodies of the present invention, all without departing from either the spirit or scope of the present invention.

What is claimed is:
1. Cys-His-Glu-Val-Asp-Lys-Asp-Ile-Ser-Gln-Leu-Gly.
2. Cys-Ala-Gln-Asn-Arg-Arg-Gly-Leu-Asp-Leu-Leu-Gly.
3. Cys-Ile-Leu-Gln-Glu-Arg-Pro-Pro-Leu-Glu-Asn-Gly.
4. Cys-His-Glu-Val-Asp-Lys-Asp-Ile-Ser-Gln-Leu-Gly and Cys-Ala-Gln-Asn-Arg-Arg-Gly-Leu-Asp-Leu-Leu-Gly.
5. Cys-His-Glu-Val-Asp-Lys-Asp-Ile-Ser-Gln-Leu-Gly and Cys-Ile-Leu-Gln-Glu-Arg-Pro-Pro-Leu-Glu-Asn-Gly.
6. Cys-Ala-Gln-Asn-Arg-Arg-Gly-Leu-Asp-Leu-Leu-Gly and Cys-Ile-Leu-Gln-Glu-Arg-Pro-Pro-Leu-Glu-Asn-Gly.
7. Cys-His-Glu-Val-Asp-Lys-Asp-Ile-Ser-Gln-Leu-Gly and Cys-Ala-Gln-Asn-Arg-Arg-Gly-Leu-Asp-Leu-Leu-Gly and Cys-Ile-Leu-Gln-Glu-Arg-Pro-Pro-Leu-Glu-Asn-Gly.
8. Cys-His-Glu-Val-Asp-Lys-Asp-Ile-Ser-Gln-Leu-Gly, Cys-Ala-Gln-Asn-Arg-Arg-Gly-Leu-Asp-Leu-Leu-Gly, Cys-Ile-Leu-Gln-Glu-Arg-Pro-Pro-Leu-Glu-Asn-Gly, and actual determinant portion of any of the foregoing which reacts with naturally occuring human immunoglobulin.

* * * * *